(12) United States Patent
Pusch et al.

(10) Patent No.: US 10,632,002 B2
(45) Date of Patent: *Apr. 28, 2020

(54) ORTHOPEDIC KNEE JOINT AND METHOD FOR CONTROLLING AN ORTHOPEDIC KNEE JOINT

(71) Applicant: OTTO BOCK HEALTHCARE GMBH, Duderstadt (DE)

(72) Inventors: Martin Pusch, Duderstadt (DE); Philipp Kampas, Vienna (AT)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/372,038

(22) Filed: Dec. 7, 2016

(65) Prior Publication Data

US 2017/0095354 A1 Apr. 6, 2017

Related U.S. Application Data

(60) Continuation of application No. 13/546,837, filed on Jul. 11, 2012, now abandoned, which is a division of application No. 12/866,698, filed as application No. PCT/DE2009/000162 on Feb. 5, 2009, now Pat. No. 8,814,948.

(30) Foreign Application Priority Data

Feb. 7, 2008 (DE) .................. 10 2008 008 284

(51) Int. Cl.
*A61F 2/68* (2006.01)
*A61F 2/64* (2006.01)
*A61F 2/70* (2006.01)
*A61F 2/50* (2006.01)
(Continued)

(52) U.S. Cl.
CPC .............. *A61F 2/64* (2013.01); *A61F 2/68* (2013.01); *A61F 2/70* (2013.01); *A61F 2002/5003* (2013.01); *A61F 2002/5021* (2013.01); *A61F 2002/5033* (2013.01); *A61F 2002/701* (2013.01); *A61F 2002/745* (2013.01); *A61F 2002/748* (2013.01); *A61F 2002/764* (2013.01);
(Continued)

(58) Field of Classification Search
CPC ........................ A61F 2/68; A61F 2002/6818
See application file for complete search history.

(56) References Cited

U.S. PATENT DOCUMENTS 5,181,931 A 1/1993 van de Veen
5,252,102 A 10/1993 Singer et al.
(Continued)

FOREIGN PATENT DOCUMENTS

CA 2704792 A1 5/2009
CN 1054364 9/1991
(Continued)

*Primary Examiner* — Bruce E Snow
(74) *Attorney, Agent, or Firm* — Holland & Hart, LLP

(57) ABSTRACT

The invention relates to an orthopedic knee joint, comprising an upper part (2), on which upper connecting means (20) are disposed, a lower part (3) pivotally supported on the upper part (2), connecting means for orthopedic components (4), and a stop ( ) for delimiting an extension movement, wherein the stop (7) is configured displaceably and coupled to an adjusting device (64), which is coupled to a control device (6), which actuates the adjusting device (64) as a function of sensor data and changes the position of the stop (7).

19 Claims, 5 Drawing Sheets

(51) Int. Cl.
   *A61F 2/74* (2006.01)
   *A61F 2/76* (2006.01)
(52) U.S. Cl.
   CPC .............. *A61F 2002/7625* (2013.01); *A61F 2002/7635* (2013.01)

(56) References Cited

U.S. PATENT DOCUMENTS

| | | | |
|---|---|---|---|
| 5,383,939 | A | 1/1995 | James |
| 6,423,098 | B1 | 7/2002 | Biedermann |
| 6,558,340 | B1 | 5/2003 | Traeger |
| 6,719,806 | B1 | 4/2004 | Zahedi et al. |
| 6,755,870 | B1 | 6/2004 | Biedermann et al. |
| 8,083,807 | B2 | 12/2011 | Auberger et al. |
| 2008/0039756 | A1 | 2/2008 | Thorsteinsson et al. |
| 2010/0305716 | A1 | 12/2010 | Pusch et al. |

FOREIGN PATENT DOCUMENTS

| | | |
|---|---|---|
| CN | 1297718 A | 6/2001 |
| CN | 1348744 | 5/2002 |
| DE | 4004988 A1 | 8/1991 |
| DE | 19859931 A1 | 7/2000 |
| DE | 69918273 T2 | 7/2005 |
| EP | 0549855 A2 | 7/1993 |
| JP | H05146 | 1/1993 |
| JP | 05-212070 | 8/1993 |
| JP | 11-019105 | 1/1999 |
| JP | 2001-511052 | 8/2001 |
| JP | 2011-502593 | 1/2011 |
| RU | 2054906 C1 | 2/1996 |
| RU | 2076670 C1 | 4/1997 |
| RU | 2096026 C1 | 11/1997 |
| WO | 03003953 A1 | 1/2003 |
| WO | 2005037151 A1 | 4/2005 |
| WO | 2009059594 A2 | 5/2009 |

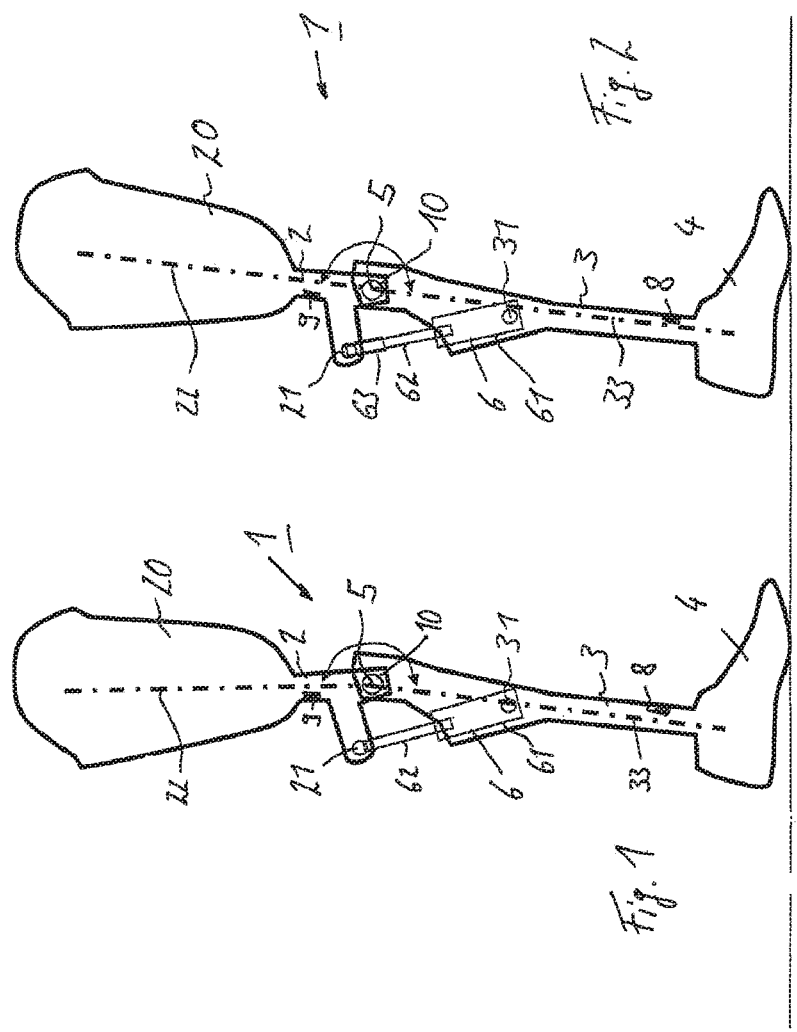

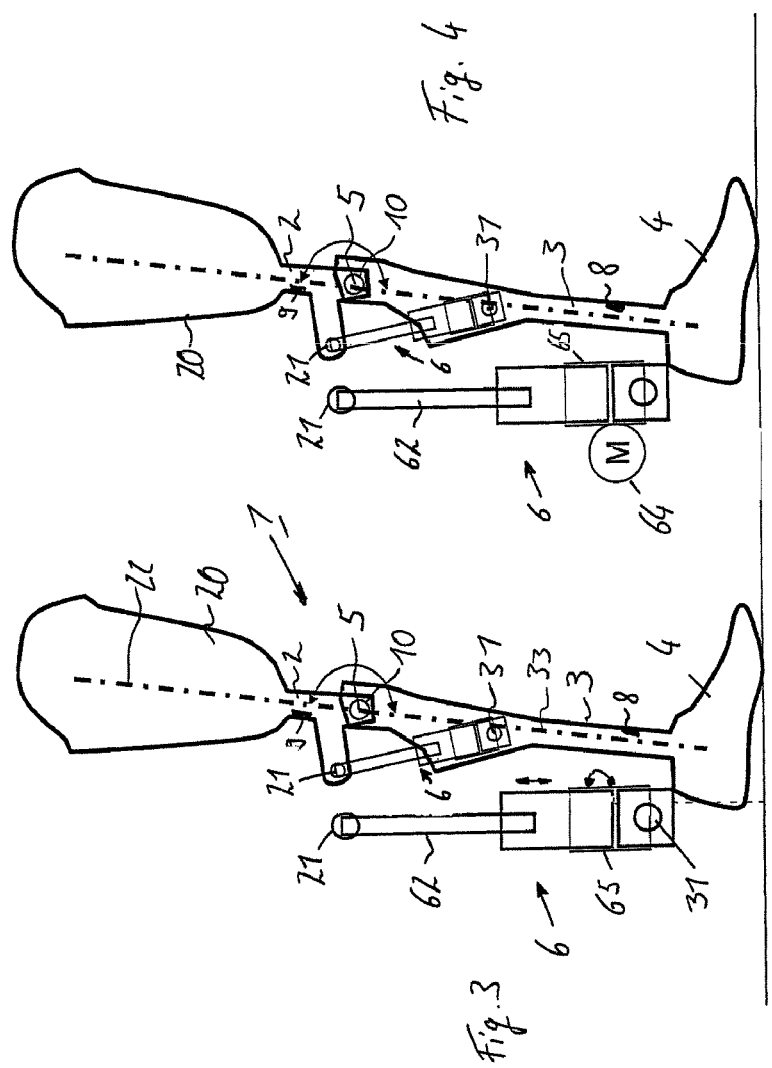

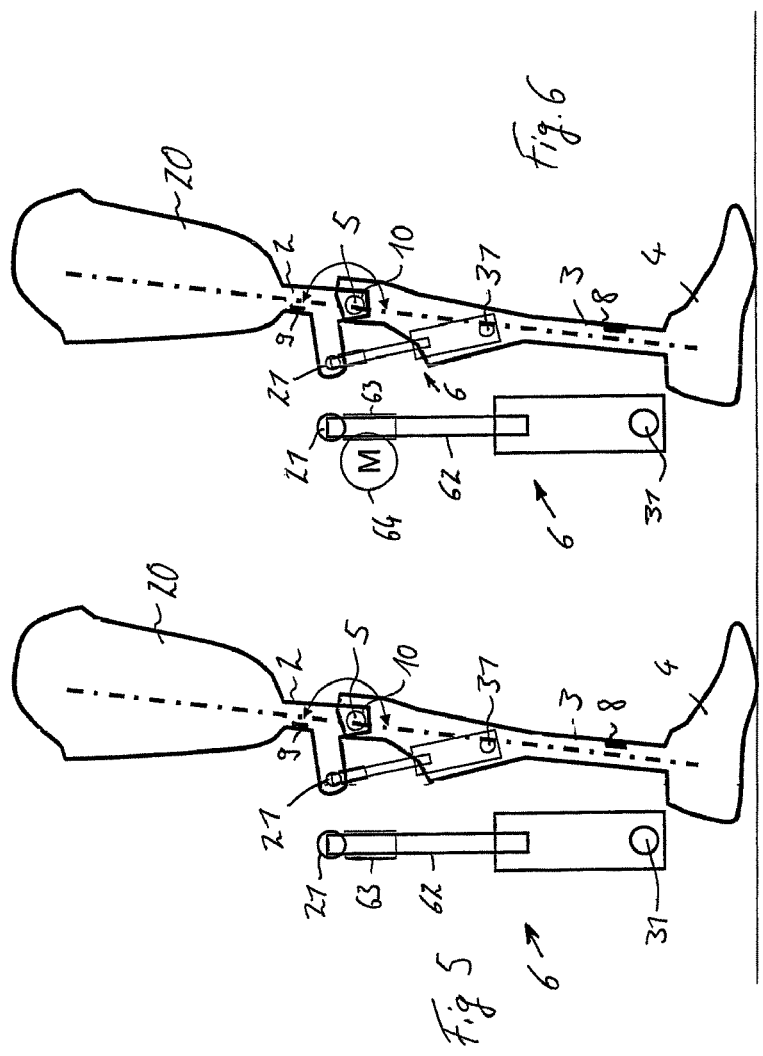

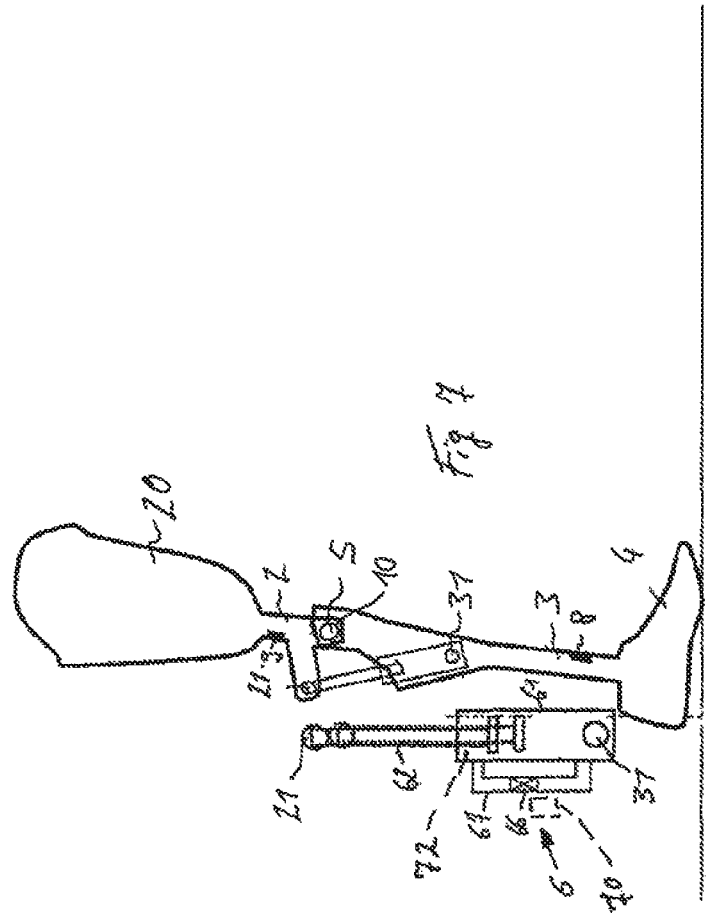

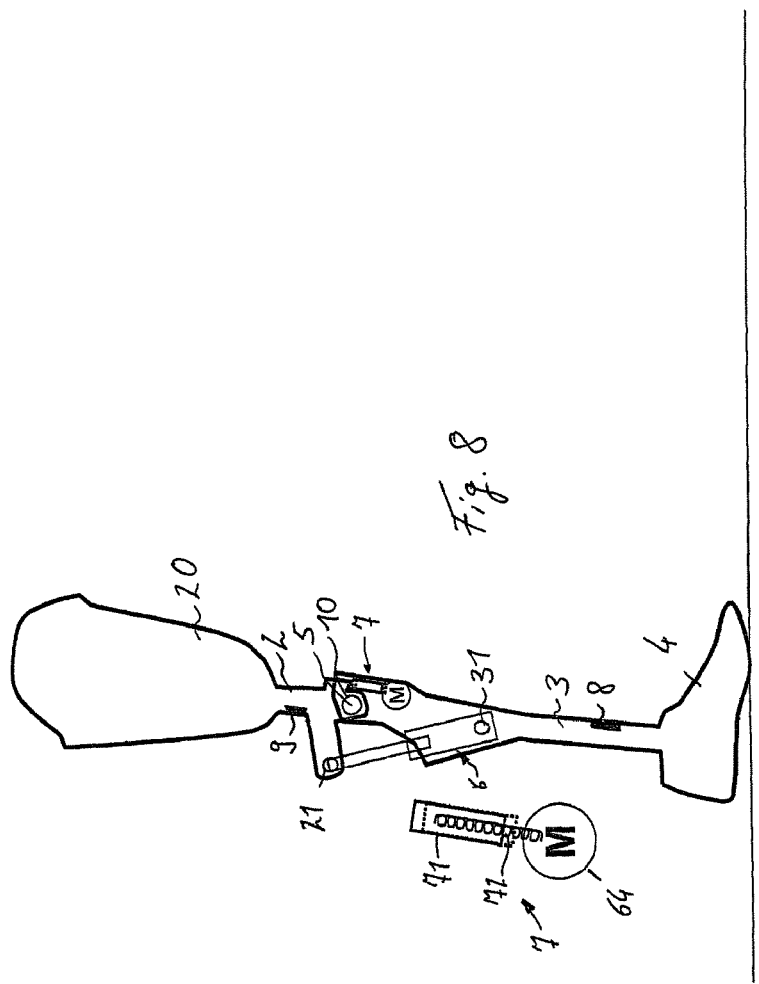

ORTHOPEDIC KNEE JOINT AND METHOD FOR CONTROLLING AN ORTHOPEDIC KNEE JOINT

CROSS-REFERENCE TO RELATED APPLICATION

This application is a continuation application of application Ser. No. 13/546,837, filed Jul. 11, 2012, abandoned, which is a division of application Ser. No. 12/866,698, filed Dec. 13, 2010, issued as U.S. Pat. No. 8,814,948, on Aug. 26, 2014, which is a 371 of PCT/DE2009/000162 filed on Feb. 5, 2009 and published on Aug. 13, 2009 as WO 2009/097841, which claims priority to German Patent Application No. 10 2008 008 284.8, filed Feb. 7, 2008, the disclosure of each of which is incorporated, in its entirety, by reference.

TECHNICAL FIELD

The invention relates to an orthopedic knee joint, with an upper part on which upper connecting means are arranged, with a lower part which is mounted pivotably on the upper part and has connecting means for prosthetic components, and with a stop for limiting an extension movement, and also a method for controlling an orthopedic knee joint.

BACKGROUND

The main aim of fitting a prosthesis is to provide the best possible replacement for the lost limb, as far as possible without functional limitations. If a patient has to be provided with an above-knee prosthesis having a prosthetic knee joint, there are many possible ways of designing such a prosthetic knee joint.

A simple passive, monocentric knee joint is particularly simple in terms of design and production, but it only partially simulates the natural knee joint and, in particular, does not permit a natural gait pattern. A securing against buckling of the prosthetic knee joint can be achieved by a suitably stable set-up, that is to say the relationship of the individual prosthesis components to one another and to the body, if appropriate assisted by a locking mechanism in what is called a lockable knee joint. In such a prosthetic knee joint, the knee is always fully extended to the end of the swing phase, as a result of which the monocentric knee joints, because of the need for a statically secure set-up, have no tendency or only a slight tendency to bend, even at the moment of heel strike. This has the effect that the impact load at heel strike is introduced directly into the thigh stump or into the hip, whereas, from the physiological point of view, the natural knee joint flexes by ca. 25° at heel strike, which results in a considerable damping of the heel strike.

In addition to monocentric prosthetic knee joints, there are polycentric prosthetic knee joints which, with a suitably high position of the instantaneous center of rotation of the extension position, have excellent inherent stability not only during standing, but also when a load is placed on the heel at the start of the stance phase of walking, with the result that the prosthetic knee joint is secure in the extended position, even without a hip extension moment being applied. A polycentric prosthetic knee joint of this type likewise permits a smooth transfer into the swing phase and an initiation of a knee flexion with loading on the front of the foot. An approximation to the natural gait pattern is thereby achieved. Polycentric prosthetic knee joints often have damping devices with which it is possible to initiate an elastically cushioned or damped flexion of the knee without loss of stability. A polycentric prosthetic knee joint with an adjustable pivot stop is described in DE 40 04 988 A1.

Furthermore, so-called active prosthetic knee joints are known which, with the aid of a motor, initiate the flexion and extension on the basis of sensor data. There are also active damping devices present in order to adapt the damping to the particular requirements. Such prosthetic knee joints are extremely complicated in terms of design and production.

SUMMARY

Proceeding from this prior art, the object of the invention is to make available a cost-effective prosthetic knee joint and a method for controlling a prosthetic knee joint, which prosthetic knee joint and which method allow the user to walk comfortably and to stand in a relaxed manner.

According to the invention, this object is achieved by an orthopedic knee joint having the features of claim 1, and by a method for controlling the orthopedic knee joint and having the features of claim 7. Advantageous embodiments and developments of the invention are described in the respective dependent claims.

The orthopedic knee joint according to the invention, with an upper part on which upper connecting means are arranged, with a lower part which is mounted pivotably on the upper part and has connecting means for prosthetic components, and with a stop for limiting an extension movement, is characterized in that the stop is designed to be movable and is coupled to an adjusting device, which is coupled in turn to a control device that actuates the adjusting device as a function of sensor data and changes the position of the stop. An orthopedic knee joint is understood to mean prosthetic knee joints and also orthotic knee joints. Where knee joints are stated below, this means orthotic and prosthetic knee joints, whereas natural knee joints are specified separately as such. If a knee joint, in particular a single-axis knee joint, is provided with an adjustable extension stop position, the extension stop can be shifted forward for walking, which results in a greater inclination at heel strike in order to flex the knee joint and, therefore, increased damping upon initiation of the stance phase. For standing, the adjusting device can be activated in such a way that the extension stop is reversed, such that a statically more secure orthosis or prosthesis set-up can be obtained. By means of the active adjustment of the active position of the extension stop, the user can be provided with a comfortable walking pattern, as a result of the dynamic forward shift and the damping of the heel strike, and with a relaxed stance, as a result of a more secure set-up.

The adjusting device advantageously has an electric motor, for example a stepping motor, which, with suitable actuation, permits a very precise positioning of the stop as a function of the sensor data.

Alternatively, the adjusting device can adjust the stop hydraulically, such that, by virtue of the basic damping properties of a hydraulic adjusting system, a damping of the stop is obtained at the same time. In the case of a purely electromotive adjustment, the stop can likewise be equipped with a stop damper in order to reduce the load on the mechanical components of the knee joint and also on the thigh stump.

The sensor data are preferably determined via sensors designed as flexion angle sensor, inclination sensor, acceleration sensor and/or force sensor, such that the data required for detection of the particular state of movement can be made available with the highest possible accuracy.

The stop can be coupled to the adjusting device via a thread, such that a spindle adjustment can take place in which either the spindle itself or the spindle nut, that is to say the inner thread or the outer thread, can be driven, such that the respective element not being directly driven moves in the corresponding direction.

Orthotic or prosthetic knee joints often have damping devices or other hydraulic devices in which a hydraulic fluid is conveyed through lines when the lower part is moved relative to the upper part. In such knee joints, the extension stop can be adjusted by a blocking device, which is arranged in the hydraulic circuit, being closed by the adjusting device when the desired or calculated angle position is reached in the extension movement. The blocking device, a throttle or a valve, can then be closed when the extension position is reached, if appropriate including the delay caused by the adjustment, such that the hydraulic fluid can no longer continue to flow, as a result of which the extension movement is stopped. The design of the extension stop as a hydraulic stop also has the advantage of being gentle on the mechanical components of the knee joint.

The method according to the invention for controlling an orthopedic knee joint with an extension stop and with an adjusting device by which the position of the extension stop can be changed is characterized in that the position of the extension stop is changed as a function of sensor data, in particular in relation to walking speed and/or stride. The walking speed and/or stride is determined via sensors, the adjustment routine or control routine being such that, at a walking speed of 0, i.e. when standing, a maximum extension is adopted in order to provide a set-up that is as secure as possible.

To use as little energy as possible and to achieve a regular gait pattern, the change of position of the extension stop is carried out during the swing phase, preferably with a continuous adjustment of the position of the end stop, which has the result that changes in the walking speed and/or stride are also taken into account. It is thus possible that the stable set-up, which is preferred during standing, is changed during walking in such a way that a knee joint dynamic in the stance phase can also contribute to the heel strike damping at quite high speeds.

The change in the position of the extension stop takes place independently of any change in the movement resistance in the flexion or extension direction. In addition to an adjustment of purely mechanical stops, which can be configured in the form of stop shoulders, pins or the like, the extension stop can also be effected by the closure of valves. The knee joints that have an adjustable damping device can be designed such that the control device, as a function of the determined sensor data, closes the extension-damping valve in a defined position of the lower part relative to the upper part, in order in this way to limit the pivoting movement. The valve is preferably designed as a shut-off valve which is closed when a predetermined position is reached. If appropriate, an adjustable throttle which is used for adapting the extension damping can be used as the shut-off valve.

BRIEF DESCRIPTION OF THE DRAWINGS

Illustrative embodiments of the invention are explained in more detail below with reference to the attached figures, in which identical reference numbers designate identical components, and in which:

FIG. 1 shows a schematic view of an above-knee prosthesis in a slightly flexed position;

FIG. 2 shows an above-knee prosthesis in a fully extended position;

FIG. 3 shows an above-knee prosthesis with a control unit whose length can be changed;

FIG. 4 shows an above-knee prosthesis according to FIG. 3 with a control unit that can be adjusted by a motor;

FIG. 5 shows an above-knee prosthesis with a coupling element whose length can be changed;

FIG. 6 shows an above-knee prosthesis with a coupling element whose length can be changed by a motor;

FIG. 7 shows an above-knee prosthesis with a coupling element that is mounted movably in a control unit; and FIG. 8 shows an above-knee prosthesis with a mechanical stop that can be adjusted by a motor.

DETAILED DESCRIPTION

FIG. 1 shows a basic set-up of an orthopedic knee joint in the form of an above-knee prosthesis 1 with an upper part 2, and with a lower part 3 in which a prosthetic foot 4 is secured. The upper part 2 and the lower part 3 are connected to each other so as to pivot about a pivot axis 5. An upper connecting means 20 in the form of a prosthesis socket is arranged at the proximal end of the upper part 2. When the orthopedic knee joint is configured as an orthosis, the connecting means are designed in the form of a shell partially enclosing the thigh or in the form of straps or other fastening means. The upper part 2 and the lower part 3 are then routed medially or laterally in relation to the natural leg, and the orthopedic component 4 is then a foot shell in which the natural foot is fitted.

A control unit 6, which has an upper fastening point 21 and a lower fastening point 31, is arranged between the upper part 2 and the lower part 3. The upper fastening point is assigned to the upper part 2, while the lower fastening point 31 is assigned to the lower part 3. The control unit 6 can be mounted in an articulated manner on the fastening points 21, 31.

In the present example, the control unit 6 has a cylinder 61 and a piston rod 62, which are mounted so as to be movable in relation to each other. The piston rod 62 is arranged on the upper fastening point 21, while the cylinder 61 is arranged on the lower fastening point 31. When the lower part 3 is pivoted, for example flexed, relative to the upper part 2, the piston rod 62 travels into the cylinder 61, and, in the case of an extension movement, the components 61, 62 travel away from each other. Within the control unit 6, it is possible to adjust the extent by which the piston rod 62 can travel out of the cylinder 61. In the position shown, the knee joint is extended to the maximum, and the longitudinal axes 22, 33 of the upper part 2 and of the lower part 3 are at an angle to each other that deviates from 180°. In the present case, the upper part 2 is flexed slightly in relation to the lower part 3, despite the fully extended prosthesis which bears on the stop formed by the piston rod 62 in the cylinder 61.

Sensors 8, 9 arranged on the lower part 3 and also on the upper part 2 are able to measure moments, forces or accelerations occurring within the prosthesis 1. Provision is likewise made that these sensors 8, 9 determine information concerning the inclination of the upper part 2 and lower part 3 either in relation to each other or in absolute terms. A flexion angle sensor 10 is likewise arranged within the knee joint 1, in the area of the pivot axis 5, in order to determine the angle position of the axes 22, 23 relative to each other and, therefore, of the upper part 2 relative to the lower part 3. These sensors 8, 9, 10 are coupled to the control device 6 such that, on the basis of the sensor data, the degree of extension can be influenced via an adjusting device (not shown), by varying the withdrawal length of the piston rod 62. The control device 6 comprises suitable data processing means which, on the basis of the existing data, calculate the position of the stop and the adjustment travel.

FIG. 2 shows a knee joint 1 that substantially corresponds to the one in FIG. 1. The piston rod 62 is here provided with a sleeve 63 which is mounted displaceably or rotatably on the piston rod 62 and via which a length adjustment can take place. If, for example, the piston rod 62 is rotated via an adjusting device, it is able to turn into or out of the sleeve 63, which is provided with a thread, in order to achieve a variation of the knee angle while the end stop remains the same within the cylinder 61. In the embodiment depicted in FIG. 2, the knee joint 1 is shown in a fully extended position, that is to say the longitudinal axes 22, 33 are at an angle of 180° to each other, which represents the preferred position during standing, since a stable set-up is achieved in this way.

The prosthesis shown in FIG. 3 differs from the one shown in FIG. 1 in that the length of the control unit 6 can be changed, for example via a screw sleeve and thread devices designed running in opposite directions to each other, such that by rotating the screw sleeve 65, which is shown on a larger scale to the left of the knee joint 1, a part of the control device 6 can be moved in the direction of the upper fastening point 21 or can be moved away from the latter, as is indicated by the double arrow. This is done by suitable rotation of the screw sleeve 65, such that the position of the stop is adjusted via the change in length of the control unit 6, and this in turn leads to a change in the maximum angle of the knee in the extended position. During this, a part of the control unit 6 coupled to the lower fastening point 31 remains fixed in position.

FIG. 4 shows that this adjustment can be carried out by electromotive means via a drive motor 64, which constitutes the adjusting device. The adjustment then takes place on the basis of a calculation within the control unit 6, which calculation is made on the basis of the data supplied by the sensors 8 to 10.

FIG. 5 shows an embodiment according to FIG. 2 together with an enlarged view of the control unit 6. The screw sleeve 65 can act on the length of the piston rod 62, i.e. of a coupling element between the lower part 3 and the upper part 2. Here too, the stop is embodied in the control unit 6, such that a change in the position of the stop can take place when the length of coupling elements between the upper part 2 and the lower part 3 changes. FIG. 6 shows that this change in the length of the coupling elements, in this case of the piston rod 62, is effected via an electric motor 64. Here too, the adjustment can take place via a rotatable threaded rod or a rotatable threaded sleeve 63 that engages in an outer thread of the piston rod 62.

FIG. 7 shows an alternative concerning the change of the stop. Here too, the stop (shown schematically with reference number 72 in FIG. 7) is embodied in the control device 6, by means of the maximum length of withdrawal of the piston rod 62 being changed. This is done by a displacement of the piston rod 62 or coupling element 62 into the cylinder 61 in the direction of the lower fastening point 31, for example by a valve 66 (also referred to as a blocking device) inside a bypass line 67 being opened such that a hydraulic fluid can pass into an upper cylinder chamber, such that the piston rod 62 can move further into the cylinder 61. At the same time, the position of the stop in the extension direction is changed, since the piston rod 62 previously abuts against the maximum stop within the cylinder 61 or presses against the hydraulic fluid. Thus, by displacement of the coupling member or piston rod 62 in the control unit 6, a limit to changed knee angles is obtained with a fully extended knee joint 1. A fully extended knee joint is present when the lower part 3 cannot be extended any further, even if an angle position of 180° is not yet reached.

An alternative embodiment is shown in FIG. 8, in which the stop is designed independently of the control unit 6 and is designed generally as a hydraulic damper unit. The separate stop 7 has the effect, via movement of a sleeve by a motor, that an end extension is achieved at different knee angles. The control signals of the electric motor 64, which forms the adjusting device, are supplied by the control device 6, which is coupled to the sensors 8 to 10. Depending on the sensor data that are determined, for example the inclination of the upper part 2 or of the lower part 3, the axial load when the foot prosthesis or foot orthosis 4 is set down, or the knee angle via the flexion angle sensor 6, different positions of the stop are adopted, such that improved adaptation to the normal gait pattern can be achieved. In FIG. 8, an adjustment of the stop sleeve 71 and of the stop 7 as a whole is effected via thread 72, which is coupled to the electric motor 64.

The observations made concerning the prosthetic knee joint 1 shown in the illustrative embodiment also apply accordingly to orthotic knee joints whose maximum angle of extension can likewise be changed as a function of sensor data.

In addition to the depicted embodiment of an adjusting device 64 as an electric motor, a hydraulic adjustment of the stop is also possible, as is indicated in FIG. 7. The valve 66 can be actuated hydraulically or electromechanically with an adjustment device 70 (shown schematically in FIG. 7), for example via a switch or a switchable valve. Further sensor devices can also be provided which, in addition to the sensor data mentioned, deliver further data to the control device. Within the control device 6, which is at the same time designed as a damper device, computing means are present which calculate a corresponding adjustment of the position of the stop and output control data for the adjusting device.

The invention claimed is:

1. A method for controlling an orthopedic knee joint, comprising:
   providing an orthopedic knee joint having an extension stop, an adjustment device, a control unit, a hydraulic damping system, and at least one sensor, the at least one sensor configured to generate sensor data;
   determining, with the control unit, a stride from the sensor data;
   automatically changing a position of the extension stop with the adjustment device, in response to control signals received from the control unit, to reduce a maximum knee angle based upon the determined stride being an increasing stride, the maximum knee angle being an angle of the knee joint measured on a rear side of the knee joint between an upper part and a lower part of the knee joint;
   wherein changing the position of the extension stop is made independent of a resistance in a flexion direction applied by the hydraulic damping system.

2. The method as claimed in claim 1, wherein the orthopedic knee joint comprises a blocking device, the method further comprising:
   closing the blocking device when an extension stop position is reached.

3. The method as claimed in claim 1, further comprising:
changing the position of the extension stop to a maximum extension position for standing.

4. The method as claimed in claim 1, further comprising:
adjusting the position of the extension stop during a swing phase.

5. The method as claimed in claim 4, further comprising:
continuously adapting the position of the extension stop.

6. The method as claimed in claim 1, wherein the orthopedic knee joint comprises a blocking device, the method further comprising:
adjusting the position of the extension stop by closing the blocking device in a hydraulic line.

7. The method as claimed in claim 1, further comprising:
measuring at least one of an acceleration occurring within the orthopedic knee joint using the at least one sensor.

8. The method as claimed in claim 1, further comprising:
calculating the position of the extension stop and an adjustment travel length.

9. The method as claimed in claim 1, further comprising:
setting a limit to the maximum knee angle when the orthopedic knee joint is fully extended.

10. The method as claimed in claim 1, wherein the sensor data includes at least acceleration sensor data.

11. The method as claimed in claim 1, wherein changing a position of the extension stop with the adjusting device includes adjusting the extension stop in a forward direction for walking and a reversed direction for standing.

12. A method for controlling an orthopedic knee joint, comprising:
providing the orthopedic knee joint with an extension stop, an adjustment device, a control unit, a hydraulic damping system, and at least one sensor;
sensing with the at least one sensor at least an acceleration associated with the orthopedic knee joint;
determining, with the control unit, a stride based at least in part on the sensing;
automatically altering a position of the extension stop with the adjustment device, in response to control signals received from the control unit, to reduce a maximum knee angle based in part upon the determined stride being an increasing stride, the maximum knee angle being an angle of the knee joint measured on a rear side of the knee joint between an upper part and a lower part of the knee joint;
wherein altering the position of the extension stop is made independent of a resistance in a flexion direction applied by the hydraulic damping system.

13. The method as claimed in claim 12, further comprising:
adopting a maximum extension stop when a walking speed is zero.

14. The method as claimed in claim 12, further comprising:
altering the position of the extension stop during a swing phase of the orthopedic knee joint.

15. The method as claimed in claim 12, wherein the extension stop is altered by closing a blocking device in a hydraulic line.

16. The method as claimed in claim 12, further comprising:
continuously altering the position of the extension stop.

17. The method as claimed in claim 12, further comprising:
providing the orthopedic knee joint with an upper part and a lower part pivotally coupled to each other;
sensing a position of the upper part relative to the lower part;
wherein the sensed position is an angled position of the upper part relative to the lower part.

18. The method as claimed in claim 12, further comprising:
calculating the position of the extension stop and an adjustment travel length.

19. The method as claimed in claim 12, further comprising:
setting a limit to the maximum knee angle when the orthopedic knee joint is fully extended.

* * * * *